(12) United States Patent
Xia et al.

(10) Patent No.: US 11,241,187 B2
(45) Date of Patent: Feb. 8, 2022

(54) ELECTROMAGNETIC WAVE SENSING AND MODULATING OF NEURONAL ACTIVITIES

(71) Applicants: Qian Xia, Singapore (SG); Xiaoping Li, Singapore (SG)

(72) Inventors: Qian Xia, Singapore (SG); Xiaoping Li, Singapore (SG)

(*) Notice: Subject to any disclaimer, the term of this patent is extended or adjusted under 35 U.S.C. 154(b) by 1473 days.

(21) Appl. No.: 14/931,869

(22) Filed: Nov. 4, 2015

(65) Prior Publication Data
US 2016/0278687 A1    Sep. 29, 2016

Related U.S. Application Data

(60) Provisional application No. 62/074,256, filed on Nov. 3, 2014.

(51) Int. Cl.
| | |
|---|---|
| *A61N 1/40* | (2006.01) |
| *A61M 21/02* | (2006.01) |
| *A61B 5/00* | (2006.01) |
| *A61B 5/0507* | (2021.01) |
| *A61B 5/16* | (2006.01) |
| *A61B 5/024* | (2006.01) |
| *A61B 5/08* | (2006.01) |
| *A61M 21/00* | (2006.01) |

(52) U.S. Cl.
CPC .......... *A61B 5/4064* (2013.01); *A61B 5/0507* (2013.01); *A61M 21/02* (2013.01); *A61N 1/40* (2013.01); *A61B 5/024* (2013.01); *A61B 5/0816* (2013.01); *A61B 5/165* (2013.01); *A61B 5/4088* (2013.01); *A61B 5/4094* (2013.01); *A61B 5/4809* (2013.01); *A61M 2021/0055* (2013.01); *A61M 2205/502* (2013.01); *A61M 2230/04* (2013.01); *A61M 2230/08* (2013.01); *A61M 2230/40* (2013.01)

(58) Field of Classification Search
CPC .................. A61N 1/40; A61M 2021/0055
See application file for complete search history.

(56) References Cited

U.S. PATENT DOCUMENTS

| | | | | |
|---|---|---|---|---|
| 3,951,134 | A * | 4/1976 | Malech | A61B 5/0006 600/544 |
| 9,456,757 | B1 * | 10/2016 | Zheng | A61B 5/031 |
| 2011/0118556 | A1 * | 5/2011 | Siegel | A61N 5/02 600/300 |
| 2011/0130800 | A1 * | 6/2011 | Weinstein | A61B 5/0402 607/17 |
| 2011/0207989 | A1 * | 8/2011 | Pilla | A61N 1/40 600/14 |
| 2011/0306962 | A1 * | 12/2011 | Schoenbach | A61B 18/12 606/34 |
| 2013/0241552 | A1 * | 9/2013 | Hirai | G01R 33/5607 324/309 |
| 2014/0243647 | A1 * | 8/2014 | Clark | A61B 5/04001 600/407 |
| 2014/0257017 | A1 * | 9/2014 | Arendash | A61N 2/02 600/14 |

(Continued)

*Primary Examiner* — Daniel J Colilla (57) ABSTRACT

The present invention presents methods and apparatus for detecting, imaging, monitoring, and modulating of brain activities and neuronal activities in the brain using radiofrequency (RF) electromagnetic (EM) waves, as well as methods and apparatus for detecting, imaging, and monitoring breathing and heart-beating using RF EM waves.

7 Claims, 7 Drawing Sheets

(56) References Cited

U.S. PATENT DOCUMENTS

2015/0057736 A1* 2/2015 Zachar .................. A61N 2/006
                                                    607/154
2015/0362574 A1* 12/2015 Wu .................... G01R 33/4835
                                                    324/322

* cited by examiner

ELECTROMAGNETIC WAVE SENSING AND MODULATING OF NEURONAL ACTIVITIES

RELATED APPLICATIONS

The present invention corresponds to the U.S. Provisional Patent Application 62/074,256, which has the title: "ELECTROMAGNETIC WAVE SENSING AND MODULATING OF NEURONAL ACTIVITIES".

FIELD OF THE INVENTION

The present invention is related to methods and apparatus for detecting, imaging, monitoring, and modulating of brain activities using radiofrequency (RF) electromagnetic (EM) waves, as well as methods and apparatus for detecting, imaging, and monitoring of breathing and heart-beat using RF EM waves.

BACKGROUND OF THE INVENTION

Brain activities are to be sensed or modulated for many important applications, such as for brain examination, monitoring or treatment, for brain-machine interfacing, and further for direct communication with the brain. So far there have been methods and apparatus for sensing of brain activities by detecting the neuronal electrical activities with needle electrodes inserted to the brain, and for sensing of brain activities by detecting the BOLD signal with functional Magnetic Resonant Imaging (fMRI), by detecting the neuronal electrical potential signals on the scalp with electroencephalography (EEG), or detecting neuronal electrical potential signals in the brain with implanted EEG or magnetoencephalography (MEG) or Positron Emission Tomography (PET). There have been Deep Brain Stimulation (DBS) as a neuromodulation technique by implanting electrodes deep in the brain to stimulate targeted brain functional site with electrical impulses for treatment of Parkinson's Disease (PD) and other movement disorders such as essential tremor and dystonia. The present invention presents methods and apparatus for detecting, imaging, monitoring and modulating of brain activities with RF EM waves, as well as detecting, imaging, and monitoring breathing rate and heart rate using RF EM waves.

BRIEF SUMMARY OF THE INVENTION

The neurons in a brain functional site are surrounding by extracellular body fluid, which is a typical dielectric by ionic polarization. The ion concentration in the extracellular fluid varies with local neuronal activation, instituting the dynamic nature of the dielectric (the extracellular fluid). In more detail, the ion concentration of the extracellular fluid surrounding the neurons varies with the neuronal activation—repolarization and depolarization, in which synchronized neuronal activations give rise to immense transmembrane ion flows, changing the ion concentration of the extracellular fluid, and therefore, changing the permittivity. Varying the ion concentration results in a dynamic nature of the dielectric (the extracellular fluid), and under an externally applied electric field, the energy taken from the applied field and stored in the dielectric in forming a polarization density varying according to the neuronal activation status from a strong state during the synchronized neuronal activation in repolarization to a weak state during the synchronized neuronal activation in depolarization and then back to a strong state, and so on. One of the features of the present invention is to detect the variation of the dielectric in association with the neuronal activations to detect and monitor the brain activities. In the present invention, the methods of detecting and monitoring of the variation of the dielectric in association with the neuronal activations can be any methods that sense the variation of the dielectric, including any RF EM wave methods that sense the variation of the dielectric.

In the present invention, a sensitive frequency method is used for using RF EM wave selectively detecting, imaging and monitoring of a targeted brain functional site. It is based on the fact that the permittivity of the dielectric (extracellular fluid) at a brain functional site is frequency dependent and there is a sensitive frequency associated with the ion concentration, shape and dimensions of the brain site; each of the brain sites must have a sensitive frequency for the RF EM wave propagating through it, with which the RF EM wave phase and amplitude changes reach the maximum when the RF EM wave propagates through the site. One of the features of the present invention is to use the sensitive frequency of a brain functional site for selectively sensing and modulating the brain site, in which the RF EM wave frequency is set at the sensitive frequency.

In the present invention, in addition to the sensitive frequency method, using the RF EM waves to selectively detect, image and monitor a targeted brain functional site can also be achieved using a focusing method, which is to transmit and receive the RF EM waves through focusing mechanisms in between the transmitting antenna and targeted brain site and between targeted brain site and receiving antenna, such that the RF EM waves emitted from the transmitting antenna is focused to propagate through the targeted brain site and is received by the receiving antenna that is also focused to the targeted brain site. The focusing mechanism can be any RF EM wave focusing mechanism, including the lens focusing and ellipsoid reflector focusing, in which the focusing ellipsoid reflector has the antenna located at one of its twin focal points and has the targeted brain site located at the other focal point.

In the present invention, one of the brain activities to be detected, imaged, and monitored using RF EM waves is the brain perception of pain. The perception of pain in the brain is to be detected, imaged and monitored to avoid anesthesia awareness during surgery, and also for objective measurement of pain in pain treatment. The brain functional site for pain perception has its activation frequency proportional to the intensity of pain. For example, when its activation frequency is below 18 Hz, the brain does not perceive pain at all; when its activation frequency is 28 Hz, the brain starts perceiving pain; as its activation frequency increases above 28 Hz and further higher, the brain perceived pain gets more and more intense. By sensing the neuronal activation frequency at the brain functional site for pain perception using RF EM waves, pain can be detected, imaged and monitored.

In the present invention, another brain activity to be detected, imaged and monitored using RF EM wave is the brain functional site for emotion, such as the amygdala. One of the applications of RF EM wave detecting, imaging and monitoring of brain emotional activities is detection of deception. Another application of such RF EM wave detecting, imaging and monitoring of brain emotional activities is rapid image triage using the brain, which has been tried by using EEG to sense brain responses to image presentation to detect brain responses to targeted images rapidly presented. The EEG can be replaced by the RF EM wave method in the present invention.

In the present invention, another brain activity to be detected, imaged and monitored using RF EM waves is seizure or epilepsy, in which the neuronal activation frequency at a part of the brain is much higher than normal and can be sensed by using the RF EM wave method in the present invention. One of the applications of RF EM wave detecting, imaging and monitoring of seizure or epilepsy is to predict the onset of seizure or epilepsy by sensing the high frequency neuronal activation in the brain using RF EM waves.

In the present invention, the activities in a brain that is in coma or vegetative states are detected, imaged and monitored using RF EM waves.

In the present invention, all kinds of brain activities are to be detected, imaged and monitored using RF EM waves for various brain-machine interface applications.

In the present invention, in addition to methods of sensing brain activities using RF EM waves, methods of neural modulation using RF EM waves are also invented. RF EM waves are normally with symmetric wave forms and do not induce an electric field in a brain when they propagate through the brain. However, when the RF EM waves are with asymmetric wave forms, such as asymmetric pulse waves rising sharply and then dropping slowly, propagating through a brain, due to the higher frequency power components in the rising part of a wave will be absorbed more than those of the lower frequency power components in the dropping part of the wave, it will generate an applied local electric field in the brain. One of the features of the present invention is to transmit an asymmetric RF EM waves propagating through the brain to generate an applied local electric field for modulating the neuronal activities in the brain.

Further in the present invention, the asymmetric pulse RF EM wave modulation of neuronal activation is selectively applied to a targeted brain functional site by having the frequency of the RF EM wave that is most sensitive to the targeted brain site, at which frequency of the RF EM wave the dielectric at the targeted brain site vary the EM wave propagating through it to the maximum.

Also in the present invention, the asymmetric pulse RF EM wave modulation of neuronal activation is selectively applied to a targeted brain functional site using a focusing method, in which the asymmetric pulse RF EM waves are applied to the targeted brain site through a focusing mechanism in between the transmitting antenna and targeted brain site such that the RF EM waves emitted from the transmitting antenna is focused to propagate to the targeted brain site. The focusing mechanism can be any EM wave focusing mechanism, including the lens focusing and ellipsoid reflector focusing, in which the focusing ellipsoid reflector has the antenna located at one of its twin focal points and has the targeted brain site at the other focal point.

One of the applications of the RF EM wave induced modulation of neuronal activation in the brain according to the present invention is for treatment of coma or vegetative state, in which asymmetric RF EM waves of a frequency that is sensitive to the targeted brain functional site, such as the reticular formation, is applied to the brain site for the treatment, which induces an electric field at the brain site to modulate the neuronal activation.

Another application of the RF EM wave induced modulation of neuronal activation in the brain according to the present invention is for treatment of coma or vegetative state, in which asymmetric RF EM waves of a frequency that is sensitive to the targeted brain functional site, such as the reticular formation, is applied to the brain site for the treatment, which induces an electric field at the brain site to modulate the neuronal activation.

In the present invention, sleep induction is achieved by applying asymmetric RF EM waves of frequency that is sensitive to the brain sleep-promoting site, Ventraliteral Periotic (VLPO), to modulate upwards the neuronal activation at the VLPO such that sleep hormones are released in the brain, getting the brain into a sleep mode. Also, in the present invention, based on that the VLPO contains warm-sensitive neurons that are more sensitive to RF EM waves than that of the neurons in the rest of the brain, the normal symmetric RF EM waves are applied to the VLPO to modulate upwards the neuronal activation frequency of the VLPO for sleep induction, in which for higher efficiency of sleep induction a low frequency pulse modulated RF EM waves are applied to the VLPO to modulate upwards the neuronal activation frequency of the VLPO for sleep induction. The modulating frequency is determined such that the sleep induction is most efficient. The pulse of the RF EM wave is determined such that the average energy input into the brain is the minimum and does not increase the brain temperature.

In the present invention, asymmetric pulse RF EM waves are applied to a targeted brain functional site, such as hypothalamus, for treatment of Alzheimer disease.

Further in the present invention, RF EM waves are used to detect, image and monitor a person's breathing and heart-beat, by transmitting the EM waves to the lung and heart, receiving the RF EM waves reflected by the lung and heart, and processing for the variations of the changes of the reflected RF EM waves in association with the movements of the lung in breathing and heart in beating, including the breathing rate and heart-beat rate.

BRIEF DESCRIPTION OF DRAWINGS

FIG. 6 shows another embodiment of the present invention—an EM wave based detecting, imaging, monitoring and modulating of neuronal activities at a brain functional site, in which in addition to the system as shown in FIG. 4, an EM wave of asymmetric wave pulse forms in burst of a modulating frequency as shown in FIG. 3 with the sensitive frequency at which the brain functional site responses to the EM wave propagating through it at the most, is transmitted together with the symmetric EM wave of the sensitive frequency into the brain, detecting the neuronal activities at the brain functional site and inducing an electric field of the modulating frequency applying to the brain functional site as the EM wave propagating through it, with which the neuronal activities at the site are detected and at the same are modulated.

DETAILED DESCRIPTION OF THE INVENTION

Figure 1:
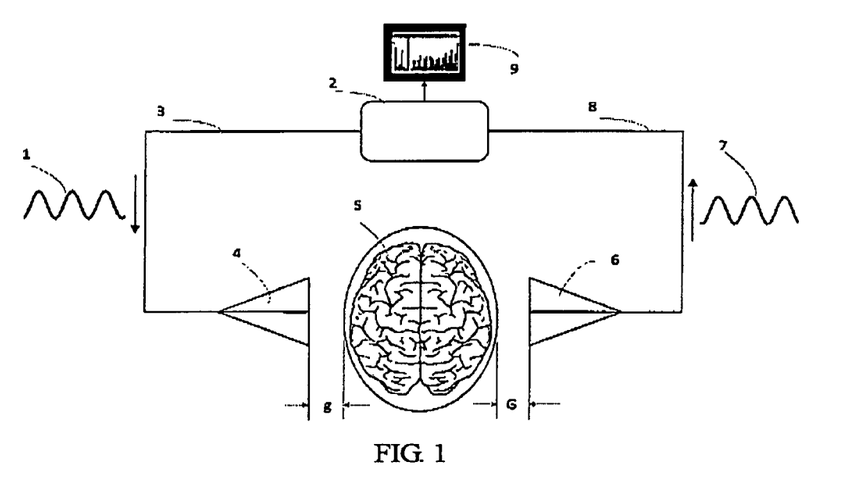
FIG. 1 shows an embodiment of the present invention—an RF EM wave based brain activity detecting, imaging and monitoring system, in which EM waves emitted from an antenna propagate through the brain, and then is received by another antenna; the phase and amplitude changes of the RF EM wave in propagating through the brain is determined and the variation of the changes in association with the neuronal activities of the brain is detected in the controller and imaged and monitored in the display panel.

As shown in FIG. 1, an RF EM wave based brain activity detecting, imaging and monitoring system, in which RF EM wave 1 is transmitted from the controller 2 via the coaxial cable 3 and transmitting antenna array 4 at a distance g from the subject brain 5, through the brain 5; the EM wave propagating through the brain 5, 7, is received by the receiving antenna array 6 at a distance G from the brain and coaxial cable 8 back to controller 1 for determining the differences between the EM wave 1 and EM wave 7 against time, so to detect the dielectric of the extracellular fluid varying against time in association with the neuronal activities in the brain, where the values of g and G are determined such that the system performs at the best. In this way, a status of neuronal activities in the brain, including illnesses of the brain, such as seizure or epilepsy, can be detected, imaged and monitored.

Figure 2:
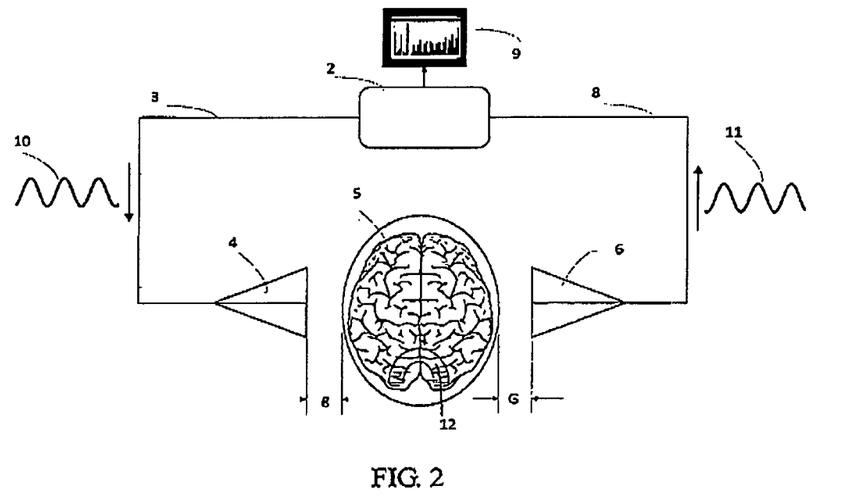
FIG. 2 shows another embodiment of the present invention—detecting, imaging and monitoring neuronal activities at a brain functional site by transmitting through the brain RF EM waves of the sensitive frequency, at which the brain functional site affects the EM wave propagating through it to the most, and receiving only the EM wave with the sensitive frequency; selectively the neuronal activities at the brain functional site are detected, imaged, and monitored in the same way as shown in FIG. 1.

As shown in FIG. 2, in the EM wave based brain activity detecting, imaging and monitoring system as shown in FIG. 1, an EM wave 10 with the sensitive frequency, at which a targeted brain functional site 12 affects the EM wave propagating through it up to the most, is transmitted into brain 5; only the EM wave with the sensitive frequency, 11, which propagates through the brain and is changed up to the most at the targeted brain functional site 12, is received back to controller 1 for determining the differences between the EM wave 10 and EM wave 11 against time, so to detect the dielectric of the extracellular fluid varying against time in association with the neuronal activities at the brain functional site 12. In this way, neuronal activities at a targeted brain functional site, such as at the motor cortex and amygdala, can be detected, imaged and monitored.

Figure 3:
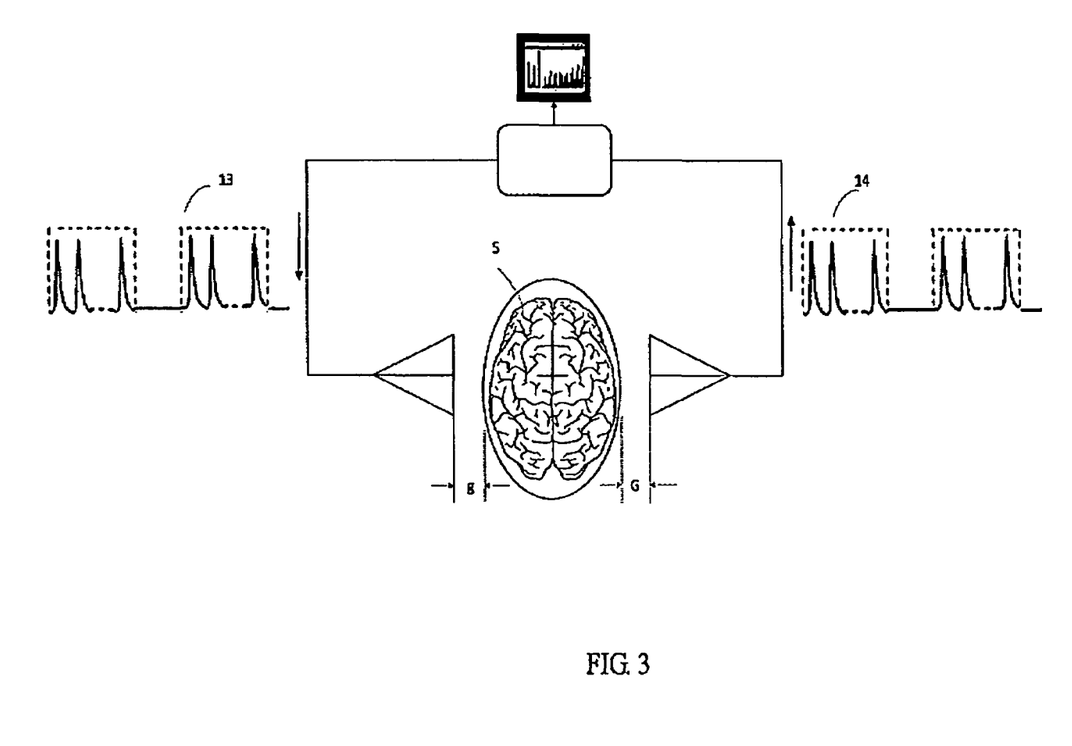
FIG. 3 shows another embodiment of the present invention—an RF EM wave system modulating neuronal activities in the brain by transmitting into the brain asymmetric pulse RF EM waves in burst of a modulation frequency, in which asymmetric pulse EM wave in burst of a modulating frequency propagating through the brain induces an electric field of the modulating frequency in the brain, modulating the neuronal activities in the brain.

As shown in FIG. 3, in the EM wave based brain activity detecting, imaging and monitoring system as shown in FIG. 1, the EM wave is replaced with asymmetric pulse waves in burst at a modulating frequency, 13, is transmitted into brain 5; the asymmetric pulse EM wave 13 propagating through brain 5 and induces an electric field of the modulating frequency applied at brain 5, modulating the neuronal activities in brain 5. In this way, the neuronal activities in brain 5, including illnesses of the brain, such as Alzheimer disease, stresses, mental fatigue, wakefulness, seizure or epilepsy, can be modulated or treated.

Figure 4:
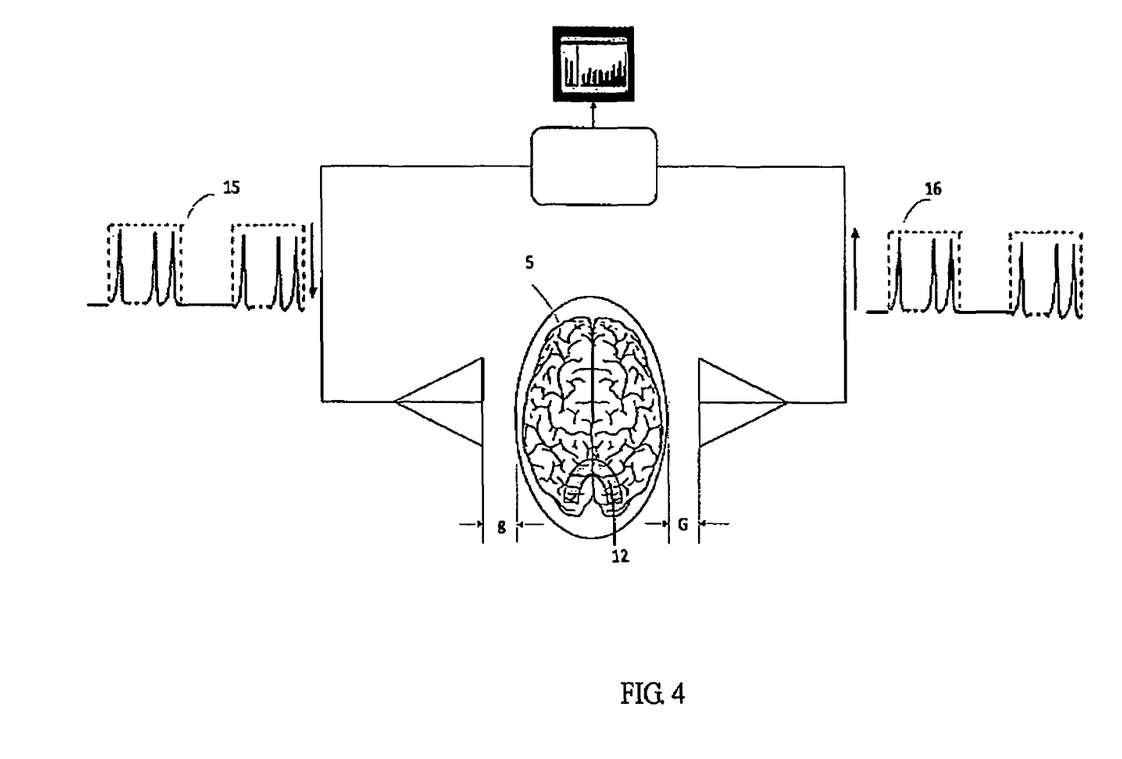
FIG. 4 shows another embodiment of the present invention—an RF EM wave system modulating neuronal activities at a targeted the brain functional site by transmitting into the brain an EM wave, with the sensitive frequency at which the brain functional site affects the EM wave propagating through it up to the most, of asymmetric pulse wave form in burst of a modulation frequency, in which asymmetric pulse EM wave in burst of a modulating frequency propagating through the brain functional site and induces an electric field of the modulating frequency at the site, modulating the neuronal activities at the site.

As shown in FIG. 4, in the EM wave based brain activity modulating system as shown in FIG. 3, when the asymmetric pulse waves in burst at a modulating frequency, 15, is with the sensitive frequency, at which the targeted brain functional site 12 affects the EM wave propagating through it up to the most, is transmitted into brain 5, the asymmetric pulse EM wave 15 propagating through brain 5 and induces an electric field of the modulating frequency applied mostly at the brain functional site 12, modulating the neuronal activities at brain functional site 12. In this way, EM wave based modulation of the neuronal activities may target at selected brain functional sites.

Figure 5:
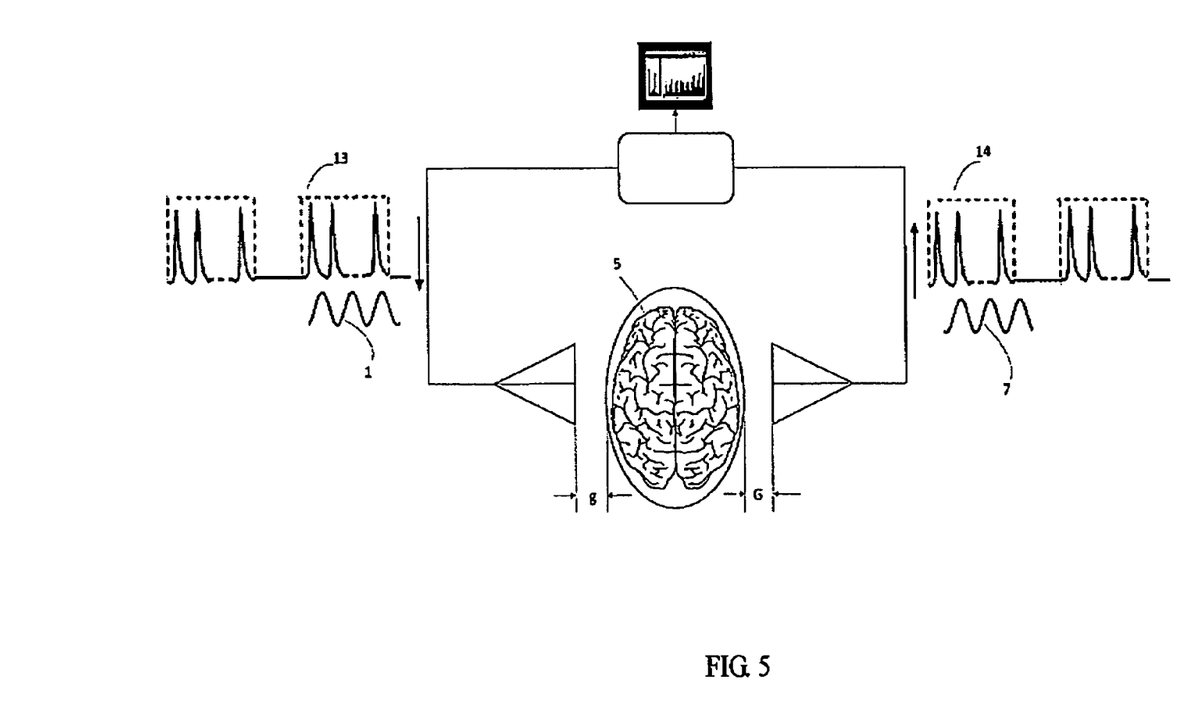
FIG. 5 shows another embodiment of the present invention—an RF EM wave based detecting, imaging, monitoring and modulating of neuronal activities in a brain, in which in addition to the system as shown in FIG. 3, symmetric RF EM waves are transmitted together with the asymmetric pulse RF EM waves into the brain, such that the neuronal activities in the brain are detected, imaged, monitored and modulated at the same time, by the symmetric RF EM waves and asymmetric pulse RF EM waves, respectively.

As shown in FIG. 5, in the EM wave based brain activity modulating system as shown in FIG. 3, a symmetric EM wave 1 is transmitted together with the asymmetric pulse EM wave 13 into brain 5, neuronal activities in brain 5 are detected, imaged, monitored and modulated at the same time. In this way, a brain illness, such as epilepsy, may be detected, treated and monitored at the same time with the same device.

Figure 6:
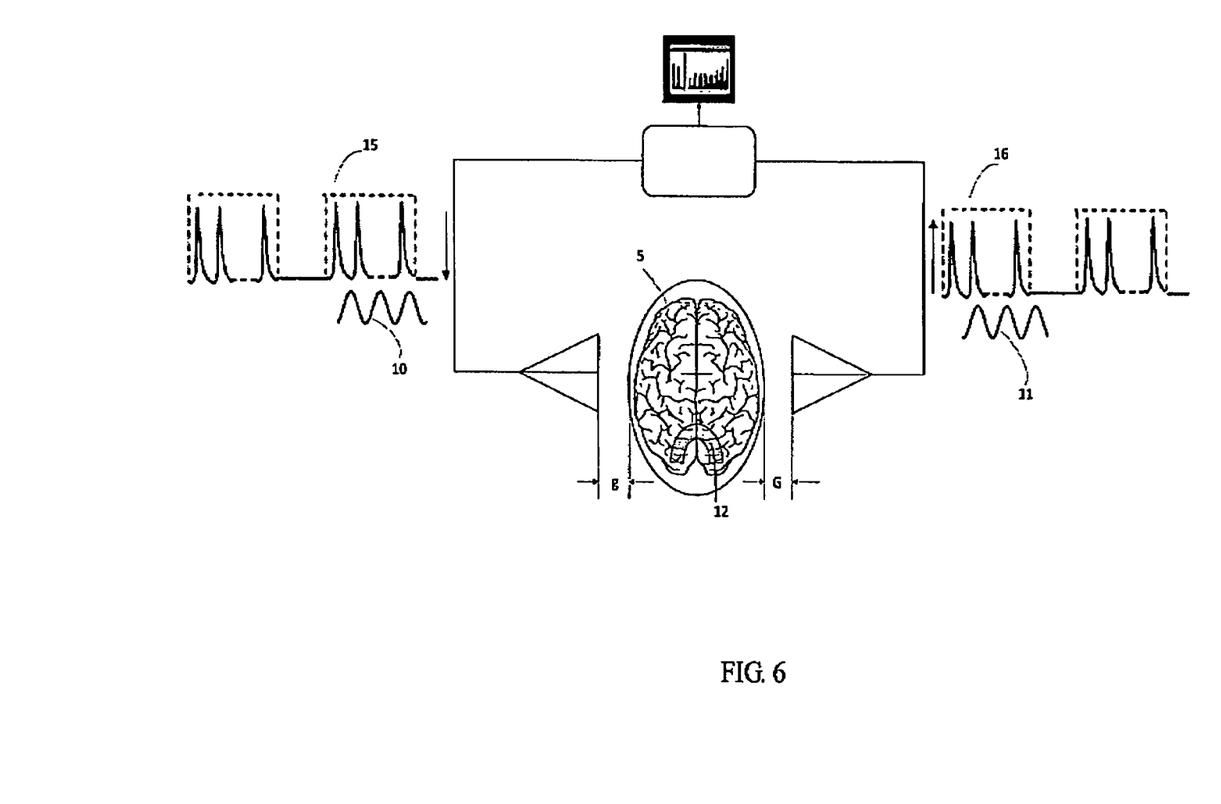

As shown in FIG. 6, in the EM wave based brain activity detecting, imaging, monitoring, and modulating system as shown in FIG. 5, when both the symmetric EM wave 10 with the sensitive frequency and asymmetric pulse EM wave 15 with the sensitive frequency are transmitted into brain 5, the neuronal activities at brain functional cite 12 are mostly detected, imaged, monitored and modulated.

Figure 7:
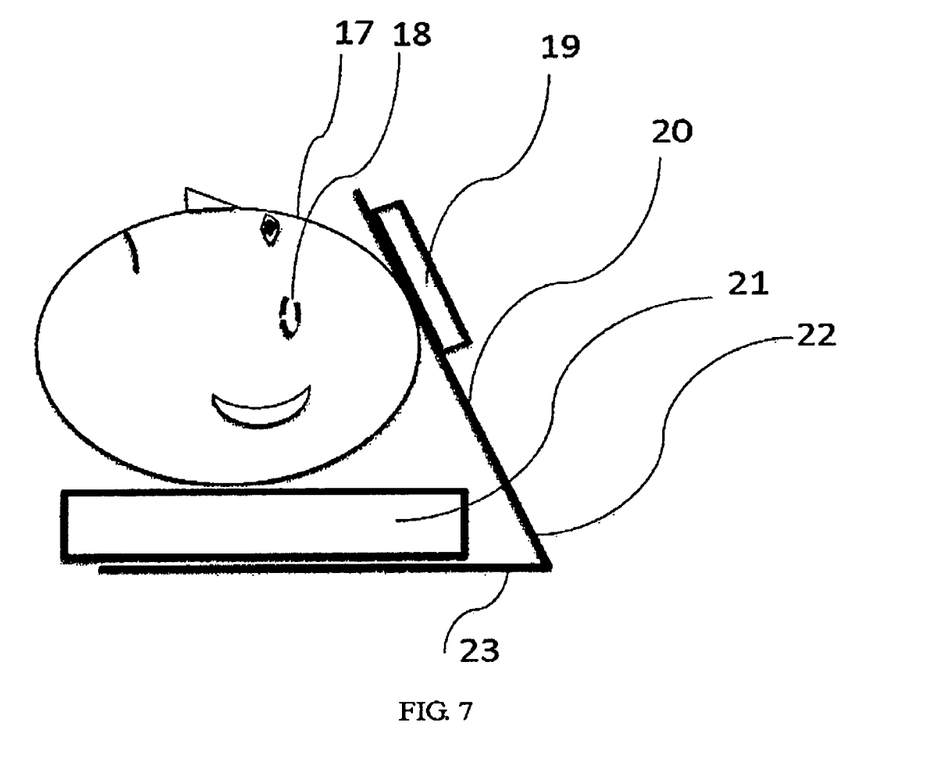
FIG. 7 shows one embodiment of the present invention, which is a device of L shape, with one arm inserted under the pillow on which a person's head is lying for sleeping, and the other arm with circuit and antenna and is standing against the head and emitting RF EM waves towards the brain sleep promoting site, VLPO, for sleep induction.

As shown in FIG. 7, a head 17 on a pillow 21 having the brain sleep-promoting site VLPO 18 received RF EM waves transmitted from antenna 19, inducing sleep hormone releasing in the brain for sleep induction.

Figure 8:
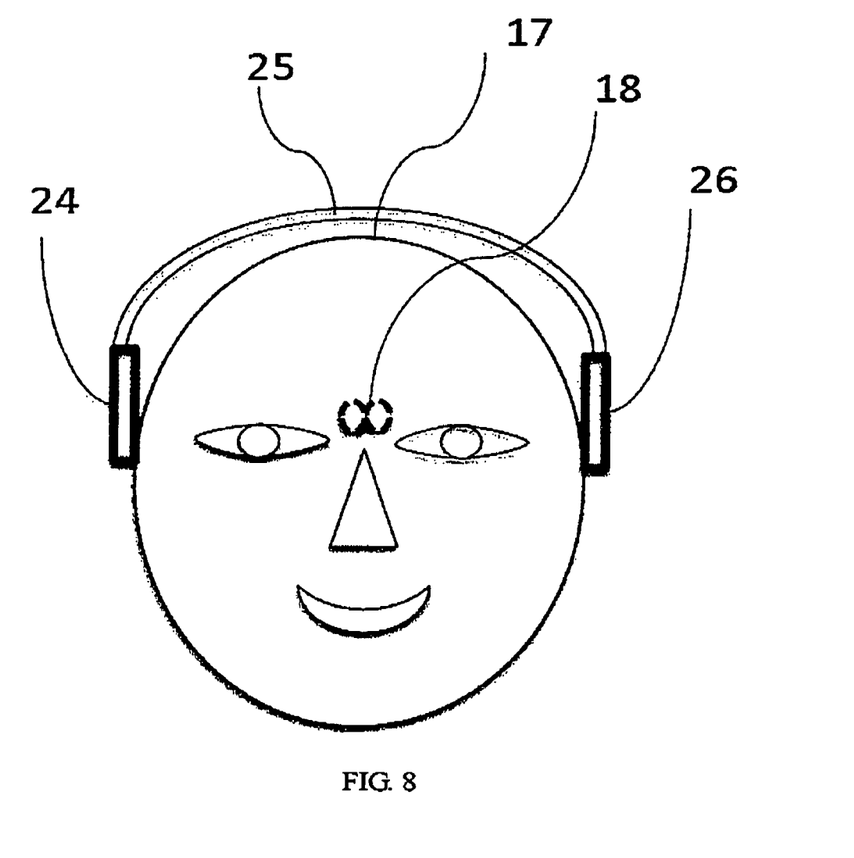
FIG. 8 shows another embodiment of the present invention, having a headband holding a circuit on top of the head and a pair of antennas each against one side of the head and emits RF EM waves towards brain sleep promoting site, VLPO, for sleep induction.

As shown in FIG. 8, a head 17 having a band 25 holding antennas 24 and 26 on each side of the head 17, and having the brain sleep-promoting site VLPO 18 received RF EM waves transmitted from antennas 24 and 26, inducing sleep hormone releasing in the brain for sleep induction.

The invention claimed is:
1. A method of modulating brain activities in a brain using RF EM waves comprising the steps of:
providing one or more electrical power sources;
providing one or more antennas;
modulating neuronal activities at a brain functional site by:
transmitting asymmetric RF EM waves through the brain functional site with said one or more antennas, wherein said one or more antennas is powered by said one or more electrical power sources; and inducing an electric field to the brain functional site;
wherein the brain functional site is a sleep promoting site, VLPO, and wherein the step of modulating neuronal activities at the VLPO releases sleep hormones in the brain, inducing the brain into a sleep mode.

2. The method of claim 1, wherein waveforms of the said asymmetric RF EM waves are pulsed waveforms with an amplitude rising rapidly and then dropping slowly or rising slowly and then dropping rapidly according to a required direction of the electric field to be induced in relation to the brain functional site.

3. The method of claim 1, wherein the neuronal activities at the brain functional site are selectively modulated by transmitting RF EM waves of a sensitive frequency of the brain functional site, which are changed the most when propagating through the brain functional site.

4. The method of claim 1, wherein the said brain activities include pain perception, coma, vegetative state, seizure, epilepsy, Alzheimer disease, emotions, stresses, mental fatigue, sleep, and wakefulness.

5. An apparatus for modulating brain activities in a brain using RF EM waves, comprising one or more electrical power sources and one or more antennas,
wherein the apparatus includes a controller configured to modulate neuronal activities at a brain functional site by transmitting asymmetric RF EM waves through the brain functional site with said one or more antennas, wherein said one or more antennas is powered by said one or more electrical power sources and induces an electric field to the brain functional site,
wherein the brain functional site is a sleep promoting site, VLPO, and the apparatus is configured to modulate neuronal activities at the VLPO to release sleep hormones in the brain, inducing the brain into a sleep mode.

6. The apparatus of claim 5, wherein the apparatus is a sleep induction device placed under a pillow, integrated with a pillow, or used as a pillow, whereby inducing the brain into a sleep mode.

7. The apparatus of claim 5, wherein the apparatus is a sleep induction device with a band for applying the sleep induction device to a head of a user whereby two or more antennas are held against the head and whereby the sleep induction device transmits RF EM waves into the brain, inducing the brain into a sleep mode.

* * * * *